United States Patent
Armstrong et al.

(10) Patent No.: US 10,405,990 B2
(45) Date of Patent: Sep. 10, 2019

(54) SPINAL IMPLANT SYSTEM AND METHOD

(71) Applicant: Warsaw Orthopedic, Inc., Warsaw, IN (US)

(72) Inventors: William D. Armstrong, Memphis, TN (US); Stanley T. Palmatier, Olive Branch, MS (US); Virginia Leigh Richardson, Memphis, TN (US); Anthony J. Melkent, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 680 days.

(21) Appl. No.: 14/835,234

(22) Filed: Aug. 25, 2015

(65) Prior Publication Data

US 2016/0067056 A1 Mar. 10, 2016

Related U.S. Application Data

(60) Provisional application No. 62/047,986, filed on Sep. 9, 2014.

(51) Int. Cl.
*A61F 2/44* (2006.01)
*A61F 2/46* (2006.01)
*A61F 2/30* (2006.01)

(52) U.S. Cl.
CPC .......... *A61F 2/4465* (2013.01); *A61F 2/4455* (2013.01); *A61F 2/4611* (2013.01); *A61F 2002/30131* (2013.01); *A61F 2002/30133* (2013.01); *A61F 2002/30471* (2013.01); *A61F 2002/30476* (2013.01); *A61F 2002/30505* (2013.01); *A61F 2002/30538* (2013.01); *A61F 2002/30836* (2013.01); *A61F 2002/4475* (2013.01)

(58) Field of Classification Search
None
See application file for complete search history.

(56) References Cited

U.S. PATENT DOCUMENTS

| | | |
|---|---|---|
| 3,061,080 A | 10/1962 | Stephen |
| 3,315,402 A | 4/1967 | Scott et al. |
| 4,328,904 A | 5/1982 | Iverson |
| 5,025,947 A | 6/1991 | Leone |
| 5,259,501 A | 11/1993 | Withers et al. |
| 5,342,365 A | 8/1994 | Waldman |
| 5,676,990 A | 10/1997 | Wawrzynski |
| 5,964,533 A | 10/1999 | Ziglar |
| 6,010,502 A | 1/2000 | Bagby |
| 6,395,031 B1 | 5/2002 | Foley et al. |
| 6,482,233 B1 | 11/2002 | Aebi et al. |
| 6,656,514 B1 | 12/2003 | Tubbs |
| 7,591,388 B2 | 9/2009 | Amormino |
| 7,875,080 B2 | 1/2011 | Puno et al. |
| 8,496,706 B2 | 7/2013 | Ragab et al. |
| 8,518,114 B2 * | 8/2013 | Marik ................... A61F 2/4425 623/17.11 |
| 2001/0035414 A1 | 11/2001 | Tyree |
| 2004/0254643 A1 | 12/2004 | Jackson |

(Continued)

*Primary Examiner* — Sameh R Boles

(57) ABSTRACT

A spinal implant comprises a body including a first vertebral engaging surface and a second vertebral engaging surface. The first vertebral engaging surface is rotatable relative to the second vertebral engaging surface. Systems and methods are disclosed.

20 Claims, 6 Drawing Sheets

(56) References Cited

U.S. PATENT DOCUMENTS

| | | |
|---|---|---|
| 2005/0252923 A1 | 11/2005 | Woolf |
| 2005/0263523 A1 | 12/2005 | Moss |
| 2007/0012701 A1 | 1/2007 | Amormino |
| 2011/0153020 A1* | 6/2011 | Abdelgany ............ A61F 2/4465 623/17.16 |
| 2013/0110238 A1 | 5/2013 | Lindemann et al. |
| 2016/0015522 A1* | 1/2016 | Arnin ...................... A61F 2/447 623/17.15 |

* cited by examiner

SPINAL IMPLANT SYSTEM AND METHOD

CROSS-REFERENCE TO RELATED APPLICATION

This application claims the benefits of U.S. Provisional Patent Application No. 62/047,986 filed Sep. 9, 2014, the contents of which being hereby incorporated in its entirety by reference.

TECHNICAL FIELD

The present disclosure generally relates to medical devices for the treatment of musculoskeletal disorders, and more particularly to a surgical system and method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, laminectomy and implantable prosthetics. As part of these surgical treatments, spinal constructs, such as, for example, bone fasteners, spinal rods and interbody devices can be used to provide stability to a treated region. For example, during surgical treatment, interbody implants and spinal constructs can be delivered to a surgical site for fixation with bone to immobilize a joint. This disclosure describes an improvement over these prior art technologies.

SUMMARY

In one embodiment, a spinal implant comprises a body including a first vertebral engaging surface and a second vertebral engaging surface. The first vertebral engaging surface is rotatable relative to the second vertebral engaging surface. In some embodiments, systems and methods are provided.

BRIEF DESCRIPTION OF THE DRAWINGS

The present disclosure will become more readily apparent from the specific description accompanied by the following drawings, in which.

DETAILED DESCRIPTION

Figure 1:
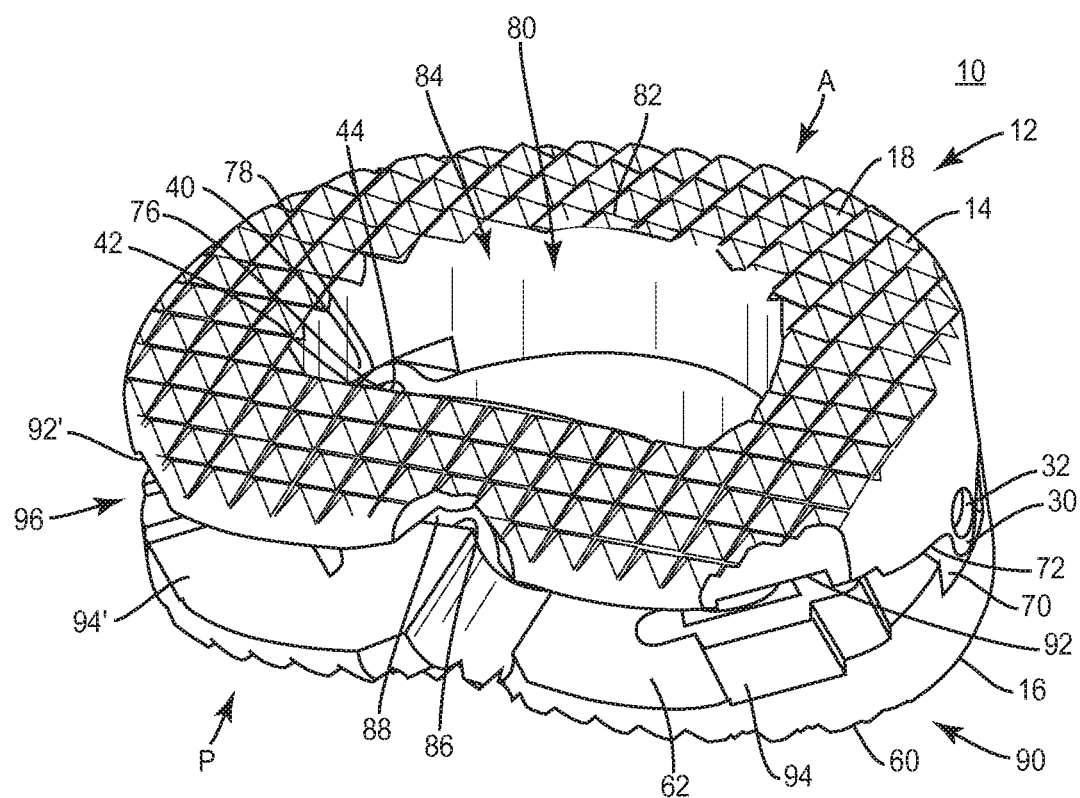
FIG. 1 is a perspective view of components of one embodiment of a system in accordance with the principles of the present disclosure.
Figure 2:
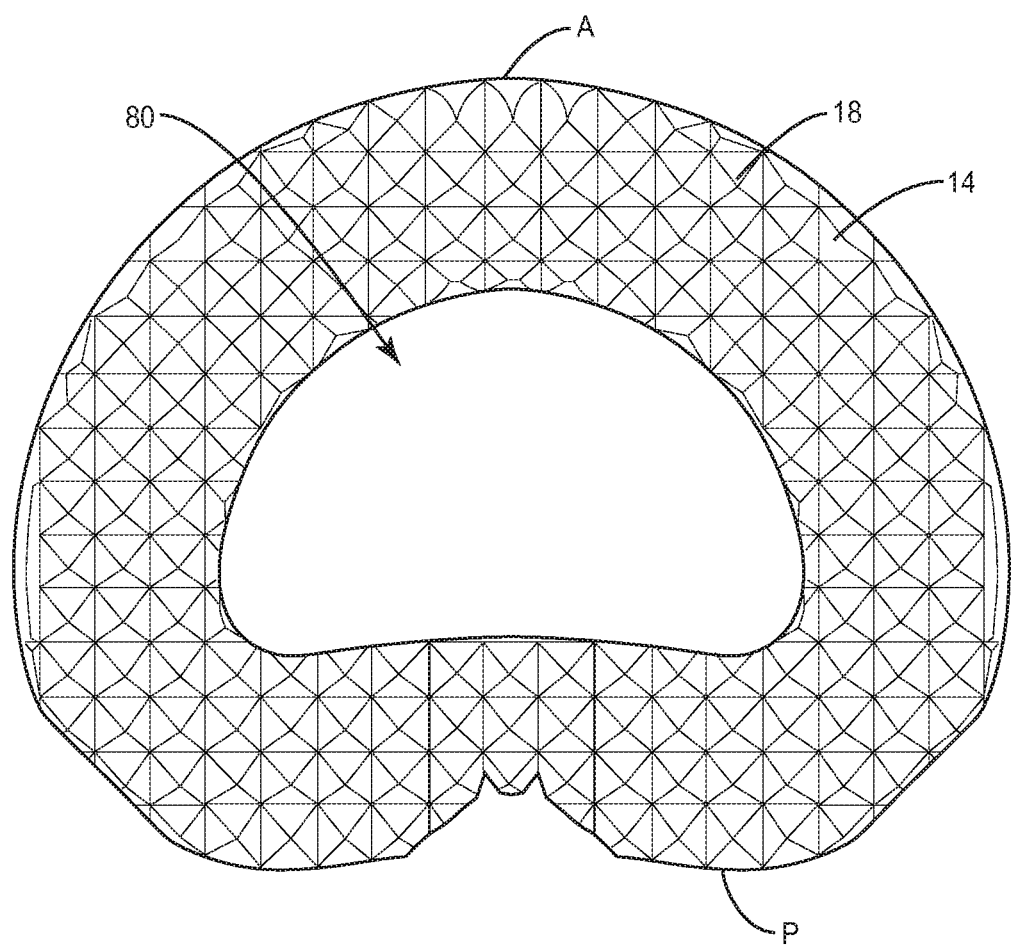
FIG. 2 is a side view of the components shown in FIG. 1.

The exemplary embodiments of the surgical system and related methods of use disclosed are discussed in terms of medical devices for the treatment of musculoskeletal disorders and more particularly, in terms of a surgical system including a spinal implant and a method for treating a spine. In one embodiment, the systems and methods of the present disclosure are employed with a spinal joint fusion, for example, with a cervical, thoracic, lumbar and/or sacral region of a spine. In one embodiment, the spinal implant includes an interbody device, a plate, spinal rods and/or bone fasteners.

In some embodiments, the present system comprises a spinal implant including at least one pedicle subtraction osteotomy (PSO) implant for use in creating and maintaining a more lordotic angle in a lumbar spine following removal of posterior bony structures of the spine.

In some embodiments, the present system comprises a spinal implant including a hinged PSO implant. In some embodiments, the present system comprises a spinal implant designed for use during a PSO procedure. In some embodiments, the present system comprises a spinal implant including a stabilizing implant that provides a variable, hinged fulcrum for restoring lordosis and height to an affected and/or selected vertebrae. In some embodiments, the present system comprises a spinal implant including a substantial bone graft pocket and can be inserted laterally, or through a posterior lumbar interbody fusion (PLIF), transforaminal lumbar interbody fusion (TLIF) and anterior lumbar interbody fusion (ALIF) approaches. In some embodiments, the present system comprises a spinal implant that can be used with an inserter attached to either end, which may include a threaded hole and inserter prong notches on each lateral end for added control.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-4, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein. In one embodiment, a spinal implant, as described herein, may be formed substantially of a biocompatible metal, such as titanium and selectively coated with a bone-growth promoting material, such as HA. In one embodiment, a spinal implant, as described herein, may be formed substantially of a biocompatible polymer, such as PEEK, and selectively coated with a biocompatible metal, such as titanium, or a bone-growth promoting material, such as HA. In some embodiments, titanium may be plasma sprayed onto surfaces of the spinal implant to modify a radiographic signature of the spinal implant and/or improve bony ongrowth to the spinal implant by application of a porous or semi-porous coating of titanium.

Spinal implant system 10 may be employed, for example, with minimally invasive procedures, including percutaneous techniques, mini-open surgical techniques and/or open surgical techniques to deliver and introduce instrumentation and/or implants, such as, for example, an interbody implant, at a surgical site within a subject body of a patient, which includes, for example, a spine. In some embodiments, the implant can include spinal constructs including one or more bone fasteners, spinal rods, connectors and/or plates. In some embodiments, various components of spinal implant system 10 may be utilized in open or traditional spinal surgical techniques.

Figure 5:
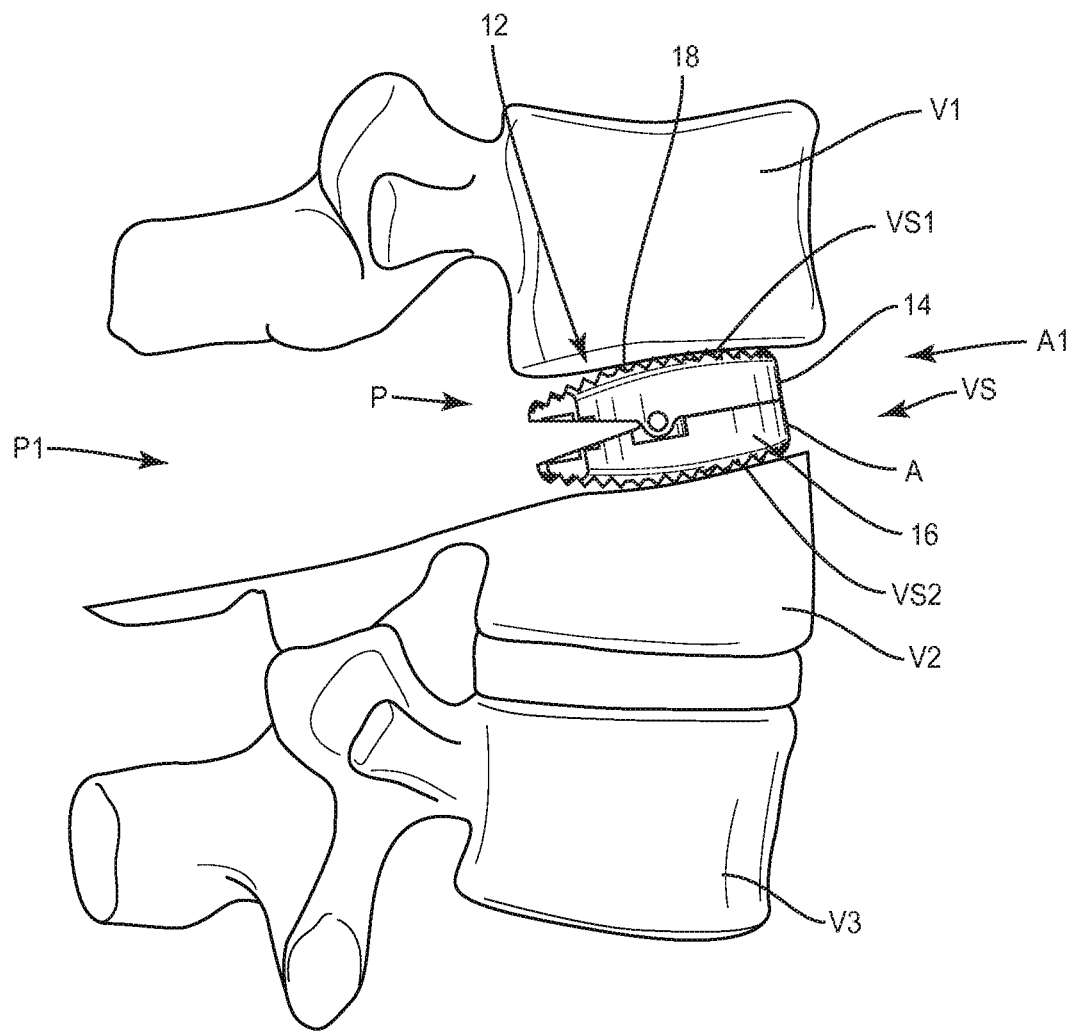
FIG. 5 is a side view of components of one embodiment of a surgical system in accordance with the principles of the present disclosure disposed with vertebrae.

Spinal implant system 10 includes an interbody implant 12. Interbody implant 12 extends between an anterior surface A and a posterior surface P. Anterior surface A is configured to face an anterior side of a body and be disposed adjacent an anterior portion of vertebrae, such as, for example, an anterior portion A1 of vertebrae V (FIG. 5). Posterior surface P is configured to face a posterior side of the body and be disposed adjacent a posterior portion of vertebrae V, such as, for example, a posterior portion P1 (FIG. 5).

Figure 3:
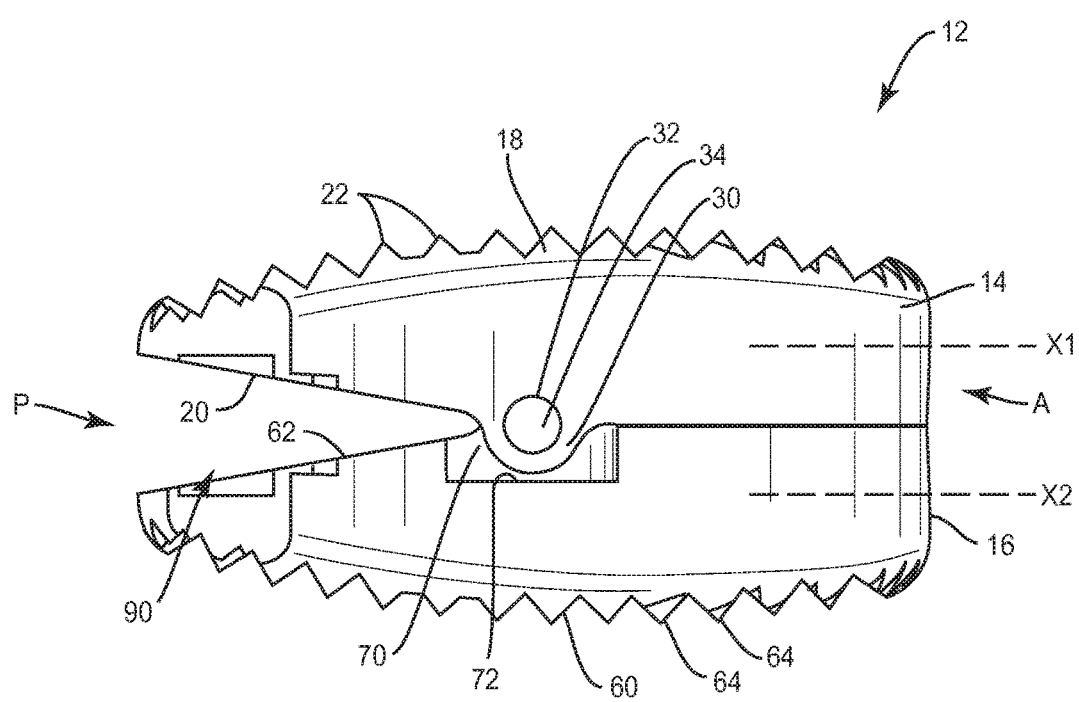
FIG. 3 is a side view of the components shown in FIG. 1.

Interbody implant 12 includes a member 14 and a member 16. Member 14 defines an axis X1, as shown in FIG. 3. Member 14 includes a vertebral engaging surface 18 and a surface 20. In some embodiments, surface 18 may be rough, textured, porous, semi-porous, dimpled, knurled, toothed, grooved and/or polished. In some embodiments, the vertebral tissue may include intervertebral tissue, endplate surfaces and/or cortical bone. Surface 18 includes tissue penetrating members, such as, for example, a plurality of teeth 22 disposed along engaging surface 18. In some embodiments, teeth 22 may have various configurations, for example, round, oval, rectangular, polygonal, irregular, tapered, offset, staggered, uniform and non-uniform.

Member 14 includes a flange 30 that defines an opening 32. Opening 32 is configured for disposal of a pin 34 configured to facilitate rotation of member 14 relative to member 16, as described herein. Opening 32 is configured for alignment and disposal with a channel 70 of member 16, as described herein. In some embodiments, the surface of member 16 that defines channel 70 includes a flange 72 defining an opening that is aligned with opening 32 and configured for disposal of pin 34 to facilitate rotation of member 14 relative to member 16, as described herein.

Member 14 includes a flange 40, disposed with an opposing side of member 14 and relative to flange 30, which includes an opening 42. Opening 42 is configured for disposal of a pin 44, configured to facilitate rotation of member 14 relative to member 16, as described herein. Opening 42 is configured for alignment and disposal with a channel 78 of member 16, as described herein. In some embodiments, the surface of member 16 that defines channel 78 includes a flange 76 defining an opening that is aligned with opening 42 and configured for disposal of pin 44 to facilitate rotation of member 14 relative to member 16, as described herein.

Member 16 defines an axis X2. Member 16 includes a vertebral engaging surface 60 and a surface 62. In some embodiments, surface 60 may be rough, textured, porous, semi-porous, dimpled, knurled, toothed, grooved and/or polished. In some embodiments, surface 60 includes tissue penetrating members, such as, for example, a plurality of teeth 64 disposed along engaging surface 60. In some embodiments, teeth 64 may have various configurations, for example, round, oval, rectangular, polygonal, irregular, tapered, offset, staggered, uniform and non-uniform.

Interbody implant 12 includes an opening 80, which is defined by the inner surfaces of members 14, 16, configured to receive an agent, which may include bone graft (not shown) and/or other materials, as described herein, for employment in a fixation or fusion treatment. In one embodiment, member 14 includes a surface 82 that defines a cavity 84 and member 16 includes a surface 86 that defines a cavity 88. Cavities 84, 88 form opening 80 that is configured to extend between surface 18 and surface 60. In some embodiments, the agent is pre-packed. In some embodiments, the agent is packed into opening 80 after interbody implant 12 is disposed with vertebrae. In some embodiments, the cross-sectional geometry of members 14, 16 may have various configurations, such as, for example, round, oval, oblong, triangular, polygonal having planar or arcuate side portions, irregular, uniform, non-uniform, consistent, variable, horseshoe shape, U-shape or kidney bean shape. In some embodiments, opening 80 can be disposed at various positions along a periphery of interbody implant 12. In some embodiments, opening 80 is positioned with interbody implant 12 such that opening 80 can be post packed with bone graft from a trajectory that interbody implant 12 was implanted. In one embodiment, interbody implant 12 is implanted from a lateral approach and opening 80 is disposed with a lateral side of interbody implant 12.

Interbody implant 12 includes a female mating portion 90 configured for engagement with surgical instrument, such as, for example, an inserter (not shown). Surface 20 defines a cavity 92 and surface 62 defines a cavity 94. Cavities 92, 94 define female mating portion 90 configured for engagement with a male portion of the inserter. In some embodiments, surface 20 defines a second cavity 92' and surface 62 defines a second cavity 94'. Cavities 92', 94' define a second female mating portion 96 configured for engagement with the male engagement portion of the inserter. In some embodiments, mating portion 90 is disposed at an angle, such as, for example, an angle of 45 degrees relative to mating portion 96 to facilitate insertion, delivery and/or positioning of interbody implant 12 adjacent to a surgical site, which may include the spine.

Member 14 is rotatable and/or pivotable relative to member 16 about pins 34, 44 such that axis X1 is rotatable and/or pivotable to one or a plurality of selected angular orientations β relative to axis X2. In some embodiments, interbody implant 12 is disposed with tissue, such as, for example, vertebrae such that surfaces 18, 60 engage vertebral tissue. In some embodiments, surfaces 18, 60 engage vertebral tissue and provide a fulcrum between the vertebral tissue surfaces. In some embodiments, surfaces 18, 60 engage vertebral tissue and passively react to forces applied to surfaces 18, 60 by the vertebral tissue such that surface 18/member 14 rotate or pivot relative to surface 60/member 16 between a first angular orientation and a second angular orientation. In some embodiments, the second angular orientation of surface 18/member 14 relative to surface 60/member 16 corresponds to a derotated, aligned, corrected and/or treated manipulation of the vertebral tissue. In some embodiments, angle β may be disposed in a range of 0-45 degrees. In some embodiments, interbody implant 12 includes a hinged fulcrum configuration including variable surface 18/member 14, surface 60/member 16 to provide a stabilizing implant that restores lordosis and height to affected and/or selected vertebrae. In some embodiments, member 14 is rotatable and/or pivotable relative to member 16 in an anterior/posterior plane such that interbody implant 12 is configured to provide for lordosis correction of vertebrae. In some embodiments, member 14 is rotatable and/or pivotable relative to member 16 in a medial/lateral plane such that interbody implant 12 is configured to provide for coronal correction of vertebrae. In some embodiments, member 14 is rotatable and/or pivotable relative to member 16 anteriorly such that interbody implant 12 is configured to provide for kyphotic correction in a thoracic spine.

In some embodiments, member 14 is rotatable and/or pivotable relative to member 16 between a first closed configuration, as shown in FIG. 3, such that members 14, 16 are disposed in flush, contacting engagement adjacent anterior portion A of interbody implant 12 and angle β is 0 degrees, and a second open configuration such that members 14, 16 are spaced apart adjacent anterior portion A and angle β is in a range of 0-45 degrees corresponding to a derotated, aligned, corrected and/or treated manipulation of the vertebral tissue. In some embodiments, interbody implant 12 is fixed in the second angular orientation via curing of bone graft. In some embodiments, interbody implant 12 is fixed in the second angular orientation via a locking element disposed with the flanges of members 14, 16. In some embodiments, interbody implant 12 is fixed in the second angular orientation via a spring element and/or resilient biasing element engaged with members 14, 16. In some embodiments, members 14, 16 are relatively rotatable and/or pivotable to an open configuration such that a gap is defined between members 14, 16 and interbody implant 12 includes a cover disposed adjacent the gap to prevent graft material from advancing past an anterior face of interbody implant 12 during a post packing procedure.

In assembly, operation and use, spinal implant system 10, similar to the systems and methods described herein, is employed during a surgical procedure, such as, for example, a PSO, a vertebral column resection (VCR) or other correction treatment to treat, for example, scoliosis and/or kyphosis of a spine. In some embodiments, one or all of the components of spinal implant system 10 can be delivered or implanted as a pre-assembled device or can be assembled in-situ. In some embodiments, one or all of the components of spinal implant system 10 may be completely or partially revised, removed or replaced.

To treat an affected section of vertebrae V, as shown in FIG. 5, a medical practitioner obtains access to a surgical site including vertebra V1, V2, V3. In some embodiments, spinal implant system 10 can be used in any existing surgical method or technique including open surgery, mini-open surgery, minimally invasive surgery and percutaneous surgical implantation, whereby a section of vertebrae V including vertebra V1-V3 are accessed through a mini-incision, or sleeve that provides a protected passageway to the area. Once access to the surgical site is obtained, the particular surgical procedure can be performed for treating the spine disorder. In some embodiments, posterior bony structure is removed from vertebrae V. In some embodiments, posterior bony structure, such as, for example, pedicle tissue is removed as part of a PSO procedure. In some embodiments, spinal implant system 10 is employed with a Grade 3 PSO procedure. In some embodiments, spinal implant system 10 is employed with a Grade 4 PSO procedure.

An incision is made in the body of a patient and a cutting instrument (not shown) creates a surgical pathway for implantation of components of spinal implant system 10. A preparation instrument (not shown) can be employed to prepare tissue surfaces VS1, VS2 of vertebrae V, as well as for aspiration and irrigation of a surgical region. In some embodiments, a portion of vertebra V2 and intervertebral disc tissue disposed between vertebrae V1, V2 is removed to define a vertebral space VS including the space between vertebral surfaces VS1, VS2, and vertebra V1 remains intact, as shown in FIG. 5. In some embodiments, vertebral space VS can include posterior portions of the spine, such as, for example, pedicles, laminae and/or spinous process. In some embodiments, a wedge portion of bone and/or other tissue is removed from a selected vertebra and adjacent intervertebral disc tissue remains intact.

In some embodiments, pilot holes are made in selected vertebra of vertebrae V for receiving fixation elements, such as, for example, bone fasteners. Each of the bone fasteners is inserted or otherwise engaged with a particular vertebra. In some embodiments, spinal constructs and rods are employed as provisional and/or working rods to support vertebrae V during a corrective procedure. In some embodiments, spinal implant system 10 may include one or a plurality of the spinal constructs. In some embodiments, the plurality of spinal constructs may be disposed in various alternate orientations, such as, for example, side by side, parallel, transverse and/or other angular orientations such as acute or obtuse, co-axial and/or may be offset or staggered. In some embodiments, the plurality of spinal constructs may provide a template configuration for permanently implantable spinal rods, such as, implantable, final, permanent, removable, non-removable, bio-absorbable, resorbable and/or bio-degradable, and/or comprise permanently implantable spinal rods.

An inserter is connected with posterior surface P to engage female engagement portion 90 and/or female engagement portion 96. The inserter delivers interbody implant 12 through the incision along the surgical pathway adjacent to the surgical site for implantation with vertebral space VS, as shown in FIG. 5. Anterior surface A of interbody implant 12 faces an anterior side of vertebrae V adjacent anterior portion A1 and posterior surface P faces a posterior side of vertebrae V adjacent posterior portion P1. In some embodiments, the inserter includes image guidance and/or surgical navigation to monitor, maintain, adjust and/or confirm disposal, delivery and/or alignment of the components of spinal implant system 10, such as, for example, interbody implant 12 along a surgical pathway and/or relative to vertebrae V.

Interbody implant 12 is disposed in a dosed configuration, as shown in FIGS. 3 and 5, such that members 14, 16 are disposed in flush, contacting engagement adjacent anterior portion A of interbody implant 12 and angle β is 0 degrees, similar to that described herein. The inserter delivers interbody implant 12 to the surgical site and vertebral space VS between vertebral surfaces VS1, VS2 such that surface 18 is disposed in a cephalad orientation of the body and surface 60 is disposed in a caudal orientation of the body. Interbody implant 12 is inserted with vertebral space VS such that teeth 22, 64 translate along vertebral surfaces VS1, VS2 for engagement of surfaces 18, 60 with the soft tissues, bone and/or fluids of vertebral surfaces VS1, VS2.

Figure 4:
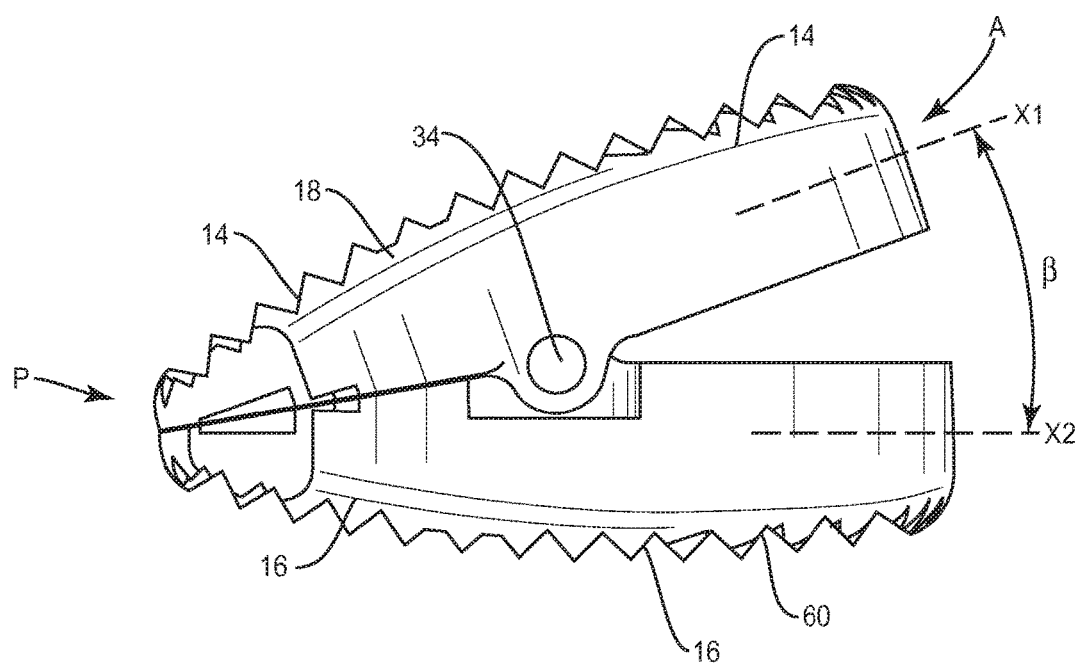
FIG. 4 is a side view of the components shown in FIG. 1.
Figure 6:
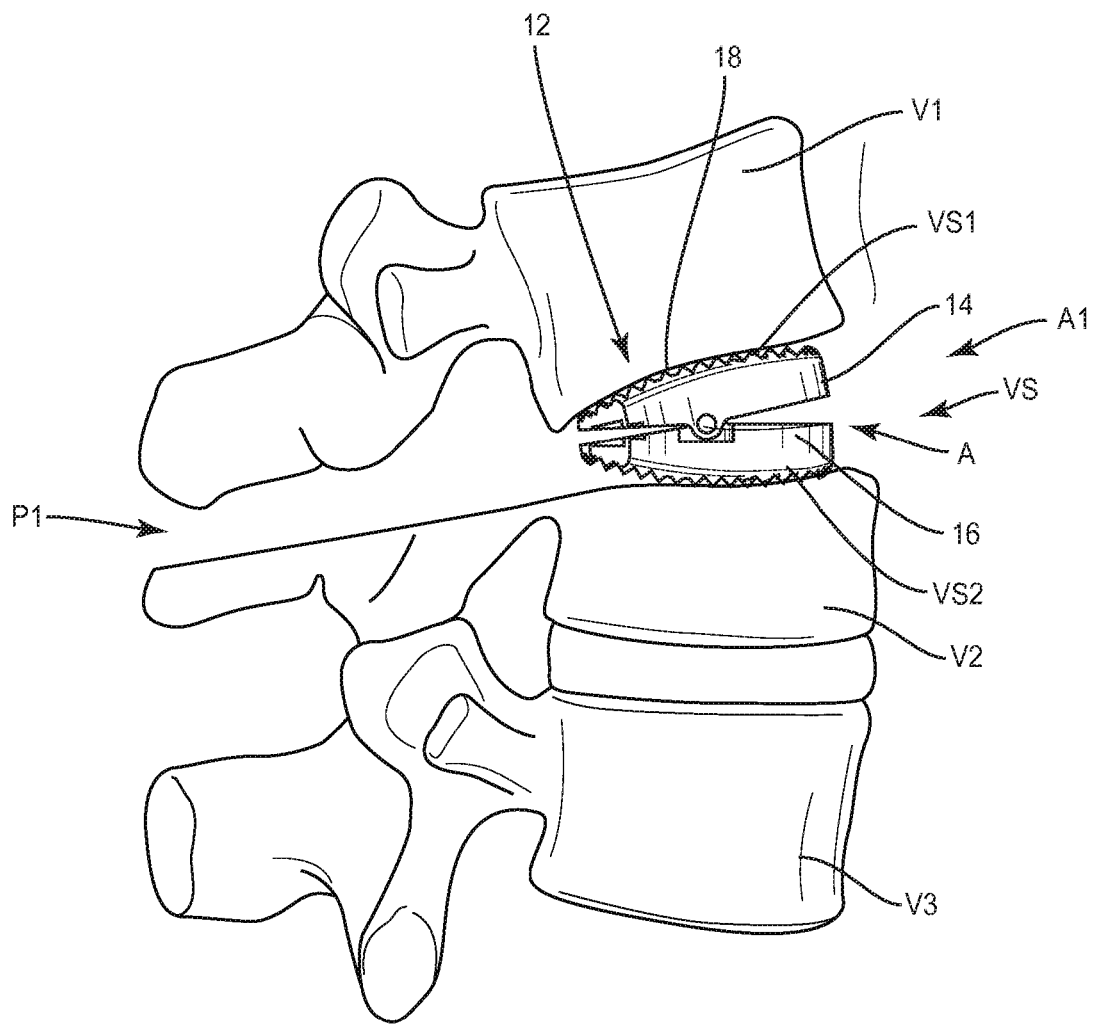
FIG. 6 is a side view of the components and vertebrae shown in FIG. 5.

Vertebrae V is derotated, aligned, corrected and/or treated via manipulation in connection with the PSO procedure. In some embodiments, the posterior aspects of vertebrae V1, V2 are collapsed and/or compressed to introduce a lordotic curve to vertebrae V. Members 14, 16 passively react to forces applied to surfaces 18, 60 by vertebral surfaces VS1, VS2 such that surface 18/member 14 rotate or pivot relative to surface 60/member 16 to an open configuration, as shown in FIGS. 4 and 6, such that members 14, 16 are spaced apart adjacent anterior portion A and angle β is in a range of 0-45 degrees, similar to that described herein, corresponding to the PSO procedure and manipulation of vertebrae V. Interbody implant 12 engages vertebral surfaces VS1, VS2 in connection with the orientation of manipulated vertebrae V to provide a hinged fulcrum configuration therebetween and a stabilizing construct that restores lordosis and height to vertebrae V including affected vertebral levels V1-V3.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiopaque markers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10. In some embodiments, spinal implant system 10 may include one or a plurality of plates, connectors and/or bone fasteners for use with a single vertebral level or a plurality of vertebral levels.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

In some embodiments, the components of spinal implant system 10 may be employed to treat progressive idiopathic scoliosis with or without sagittal deformity in either infantile or juvenile patients, including but not limited to pre-pubescent children, adolescents from 10-12 years old with continued growth potential, and/or older children whose growth spurt is late or who otherwise retain growth potential. In some embodiments, the components of spinal implant system 10 and related methods of use may be employed to prevent or minimize curve progression in individuals of various ages.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
    a body including a first plate comprising a first vertebral engaging surface and a bottom surface opposite the first vertebral engaging surface, the body including a second plate comprising a second vertebral engaging surface and a top surface opposite the second vertebral engaging surface, the body including an opening that extends through the vertebral engaging surfaces, the body comprising first and second cavities each extending into the bottom surface and third and fourth cavities each extending into the top surface, the first and third cavities being aligned to define a first female mating portion configured for engagement with a male mating portion of an inserter, the second and fourth cavities being aligned to define a second female mating portion configured for engagement with the male mating portion, the body comprising a first aperture extending into the top surface and a second aperture extending into the bottom surface, the first and second apertures defining a passageway positioned between the first female mating portion and the second female mating portion,
    wherein the first vertebral engaging surface is rotatable relative to the second vertebral engaging surface.

2. A spinal implant as recited in claim 1, wherein the first vertebral engaging surface is pivotable relative to the second vertebral engaging surface about a hinge.

3. A spinal implant as recited in claim 1, wherein the vertebral engaging surfaces each include flanges connected by opposing pin hinges such that the vertebral engaging surfaces are relatively rotatable.

4. A spinal implant as recited in claim 1, wherein the first vertebral engaging surface is pivotable relative to the second vertebral engaging surface in a range of 0 through 45 degrees.

5. A spinal implant as recited in claim 1, wherein the first vertebral engaging surface defines a first axis and the second vertebral engaging surface defines a second axis, the first axis being rotatable to a selected angular orientation relative to the second axis.

6. A spinal implant as recited in claim 5, wherein the vertebral engaging surfaces are fixed in a selected angular orientation.

7. A spinal implant as recited in claim 5, wherein the vertebral engaging surfaces are fixed in a selected angular orientation via curing of bone graft.

8. A spinal implant as recited in claim 5, wherein the vertebral engaging surfaces are fixed in a selected angular orientation via a locking element.

9. A spinal implant as recited in claim 1, wherein the vertebral engaging surfaces are relatively rotatable to a selected angular orientation via a resilient biasing element engaged with the vertebral engaging surfaces.

10. A spinal implant as recited in claim 1, wherein the vertebral engaging surfaces are relatively rotatable in an anterior/posterior plane of vertebrae.

11. A spinal implant as recited in claim 1, wherein the vertebral engaging surfaces are relatively rotatable in a medial/lateral plane of vertebrae.

12. A spinal implant as recited in claim 1, wherein the vertebral engaging surfaces are relatively rotatable between a closed configuration and an open configuration.

13. A spinal implant as recited in claim 1, wherein the vertebral engaging surfaces each include a plurality of teeth.

14. A spinal implant as recited in claim 1, wherein the vertebral engaging surfaces are relatively rotatable between a closed configuration such that the vertebral engaging surfaces are disposed in flush, contacting engagement adjacent an anterior portion of the body and an open configuration such that the vertebral engaging surfaces are spaced apart adjacent the anterior portion.

15. A spinal implant as recited in claim 1, wherein the vertebral engaging surfaces define a first mating surface and a second mating surface disposed at an angular orientation relative to the first mating surface, the mating surfaces being engageable with a surgical inserter.

16. A spinal implant as recited in claim 1, wherein the vertebral engaging surfaces define a first mating surface and a second mating surface disposed at an angle of 45 degrees relative to the first mating surface, the mating surfaces being engageable with a surgical inserter.

17. A spinal implant comprising:
    a first member extending between opposite first and second ends, the first member including a first vertebral engaging surface and a bottom surface opposite the first vertebral engaging surface, the first member including spaced apart first and second flanges that are positioned between the first and second ends;
    a second member extending between opposite first and second ends, the second member including a second vertebral engaging surface and a top surface opposite the second vertebral engaging surface, the second member including spaced apart third and fourth flanges that are positioned between the first and second ends of the second member, the vertebral engaging surfaces each including a plurality of teeth, the implant comprising first and second cavities each extending into the bottom surface and third and fourth cavities each extending into the top surface, the first and third cavities being aligned to define a first female mating portion, the second and fourth cavities being aligned to define a second female mating portion, the implant comprising a first aperture extending into the top surface and a second aperture extending into the bottom surface, the first and second apertures defining a passageway positioned between the first female mating portion and the second female mating portion;
    an opening that extends continuously between and through the vertebral engaging surfaces;
    a first pin that extends through the first flange and the third flange; and
    a second pin that extends through the second flange and the fourth flange, wherein the first member is rotatable relative to the second member about the pins.

18. A spinal implant comprising:

a first member extending along a first longitudinal axis between opposite first and second ends, the first member including a first vertebral engaging surface and a first surface opposite the first vertebral engaging surface, the first surface including a first portion that extends parallel to the first longitudinal axis and a second portion that extends transverse to the first longitudinal axis; and a second member extending along a second longitudinal axis between opposite first and second ends, the second member including a second vertebral engaging surface and a second surface opposite the second vertebral engaging surface, the second surface including a first portion that extends parallel to the second longitudinal axis and a second portion that extends transverse to the second longitudinal axis, the implant comprising first and second cavities each extending into the first surface and third and fourth cavities each extending into the second surface, the first and third cavities being aligned to define a first female mating portion, the second and fourth cavities being aligned to define a second female mating portion, the implant comprising a first aperture extending into the top surface and a second aperture extending into the bottom surface, the first and second apertures defining a passageway positioned between the first female mating portion and the second female mating portion, wherein the first vertebral engaging surface is rotatable relative to the second vertebral engaging surface between a first orientation in which the first portions directly engage one another and the second portions are spaced apart from one another and a second orientation in which the second portions directly engage one another and the first portions are spaced apart from one another.

19. A spinal implant as recited in claim 18, wherein the spinal implant comprises an opening that extends through the vertebral engaging surfaces, the first surface and the second surface.

20. A spinal implant as recited in claim 18, wherein the first member includes spaced apart first and second flanges that are positioned between the first and second portions of the first surface and the second member includes spaced apart third and fourth flanges that are positioned between the first and second portions of the second surface, the spinal implant including a first pin that extends through openings in the first and third flanges and a second pin that extends through openings in the second and fourth flanges.

* * * * *